(12) United States Patent
Okamura et al.

(10) Patent No.: US 7,313,218 B2
(45) Date of Patent: Dec. 25, 2007

(54) RADIOGRAPHIC APPARATUS AND RADIATION DETECTION SIGNAL PROCESSING METHOD

(75) Inventors: Shoichi Okamura, Nara-ken (JP); Keiichi Fujii, Kyoto-fu (JP); Susumu Adachi, Osaka-fu (JP); Shinya Hirasawa, Kyoto-fu (JP); Toshinori Yoshimuta, Osaka-fu (JP); Koichi Tanabe, Kyoto-fu (JP); Shigeya Asai, Kyoto-fu (JP); Akihiro Nishimura, Kyoto-fu (JP)

(73) Assignee: Shimadzu Corporation, Kyoto-fu (JP)

( * ) Notice: Subject to any disclaimer, the term of this patent is extended or adjusted under 35 U.S.C. 154(b) by 307 days.

(21) Appl. No.: 10/901,212

(22) Filed: Jul. 29, 2004

(65) Prior Publication Data

US 2005/0031070 A1 Feb. 10, 2005

(30) Foreign Application Priority Data

Aug. 8, 2003 (JP) ............................. 2003-290332

(51) Int. Cl.
*G12K 1/12* (2006.01)
(52) U.S. Cl. ........................... 378/22; 378/19; 378/901
(58) Field of Classification Search ............ 378/21–27, 378/98.8, 189–192, 901, 19
See application file for complete search history.

(56) References Cited

U.S. PATENT DOCUMENTS

| | | | | |
|---|---|---|---|---|
| 4,000,425 A * | 12/1976 | Craig | ........................... | 378/24 |
| 5,249,123 A | 9/1993 | Hsieh | ........................... | 378/19 |
| 5,265,013 A * | 11/1993 | King et al. | ..................... | 378/4 |
| 5,359,638 A * | 10/1994 | Hsieh et al. | .................... | 378/4 |
| 5,517,544 A * | 5/1996 | Levinson | ........................ | 378/4 |
| 6,295,331 B1* | 9/2001 | Hsieh | ........................... | 378/19 |
| 6,493,646 B1* | 12/2002 | Hsieh et al. | ................. | 702/104 |
| 7,003,071 B2* | 2/2006 | Nagaoka et al. | .............. | 378/19 |
| 2003/0194058 A1* | 10/2003 | Tsujii | ........................... | 378/210 |
| 2003/0223539 A1* | 12/2003 | Granfors et al. | ........... | 378/98.8 |
| 2005/0036582 A1* | 2/2005 | Nagaoka et al. | .............. | 378/19 |
| 2005/0151086 A1* | 7/2005 | Spahn | ................... | 250/370.08 |

OTHER PUBLICATIONS

Investigation of a Solid-State Detector for Advanced Computed Tomography, Hsieh et al., IEEE Transactions on Medical Imaging, vol. 19, No. 9, Sep. 2000.*

* cited by examiner

*Primary Examiner*—Courtney Thomas
*Assistant Examiner*—Alexander Taningco
(74) *Attorney, Agent, or Firm*—Cheng Law Group PLLC

(57) ABSTRACT

A radiographic apparatus removes lag-behind parts from radiation detection signals taken from an FPD as X rays are emitted from an X-ray tube, on an assumption that the lag-behind part included in each X-ray detection signal is due to an impulse response formed of a plurality of exponential functions with different attenuation time constants. When a single attenuation time constant and intensity are provisionally set, checking is made whether an attenuation to a noise level of X-ray detection signals occurs in an X-ray non-emission state following an X-ray emission state. When the set attenuation time constant and intensity are found appropriate (OK), the impulse response having the single exponential function is determined valid. Corrected radiation detection signals are obtained by removing the lag-behind parts using the impulse response determined.

20 Claims, 8 Drawing Sheets

RADIOGRAPHIC APPARATUS AND RADIATION DETECTION SIGNAL PROCESSING METHOD

BACKGROUND OF THE INVENTION (1) Field of the Invention

This invention relates to a radiographic apparatus for medical or industrial use and a radiation detection signal processing method, for obtaining radiographic images based on radiation detection signals fetched at predetermined sampling time intervals by a signal sampling device from a radiation detecting device as radiation is emitted from a radiation emitting device. More particularly, the invention relates to a technique for determining a time constant and intensity of an exponential function forming an impulse response of the radiation detecting device.

(2) Description of the Related Art

In a medical fluoroscopic apparatus which is a typical example of radiographic apparatus, a flat panel X-ray detector (hereinafter called "FPD" as appropriate) has recently been used as an X-ray detecting device for detecting X-ray penetration images of a patient resulting from X-ray emission from an X-ray tube. The FPD includes numerous semiconductor or other X-ray detecting elements arranged longitudinally and transversely on an X-ray detecting surface.

That is, in the fluoroscopic apparatus, X-ray detection signals for one X-ray image are taken at sampling time intervals from the FPD as a patient is irradiated with X rays from the X-ray tube. The fluoroscopic apparatus is constructed to obtain, based on the X-ray detection signals, an X-ray image corresponding to an X-ray penetration image of the patient for every period between sampling intervals. The use of the FPD is advantageous in terms of apparatus construction and image processing since the FPD is lighter and less prone to complicated detecting distortions than the image intensifier used heretofore.

However, the FPD has a drawback of causing time lags whose adverse influence appears in X-ray images. Specifically, when X-ray detection signals are taken from the FPD at short sampling time intervals, the remainder of a signal not picked up adds to a next X-ray detection signal as a lag-behind part. Thus, where X-ray detection signals for one image are taken from the FPD at 30 sampling intervals per second to create X-ray images for dynamic display, the lag-behind part appears as an after-image on a preceding screen to produce a double image. This results in an inconvenience such as blurring of dynamic images.

U.S. Pat. No. 5,249,123 discloses a proposal to solve the problem of the time lag caused by the FPD in acquiring computer tomographic images (CT images). This proposed technique employs a computation for eliminating a lag-behind part from each of radiation detection signals taken from an FPD at sampling time intervals Δt.

That is, in the above U.S. patent, a lag-behind part included in each of the radiation detection signals taken at the sampling time intervals is assumed due to an impulse response formed of a plurality of exponential functions, and the following equation is used to derive corrected radiation detection signal $x_k$ with a lag-behind part removed from radiation detection signal $y_k$:

$$X_k = [y_k - \Sigma_{n=1}^{N} \{\alpha_n \cdot [1-\exp(T_n)] \cdot \exp(Tn) \cdot S_{nk}\}] / \Sigma_{n=1}^{N} \beta_n$$

in which $T_n = -\Delta t/\tau_n$, $S_{nk} = X_{k-1} + \exp(T_n) \cdot S_{n(k-1)}$, and $\beta_n = \alpha_n \cdot [1-\exp(T_n)]$, where Δt: sampling intervals;
k: subscript representing a k-th point of time in a sampling time series;
N: the number of exponential functions with different time constants forming the impulse response;
n: subscript representing one of the exponential functions forming the impulse response;
$\alpha_n$: intensity of exponential function n; and
τn: attenuation time constant of exponential function n.

Inventors herein have tried the computation technique proposed in the above U.S. patent. However, the only result obtained is that the above technique cannot avoid artifacts due to the time lag and satisfactory X-ray images cannot be obtained. It has been confirmed that the time lag due to the FPD is not eliminated.

SUMMARY OF THE INVENTION

This invention has been made having regard to the state of the art noted above, and its object is to provide a radiographic apparatus and a radiation detection signal processing method for easily determining time lags, due to a radiation detecting device, of radiation detection signals taken from the radiation detecting device.

The following technique is conceivable to solve the above problem. In dealing with the time lag of the FPD, this technique removes a lag-behind part due to an impulse response based on the following recursive equations a-c:

$$X_k = Y_k - \Sigma_{n=1}^{N} \{\alpha_n \cdot [1-\exp(T_n)] \cdot \exp(T_n) \cdot S_{nk}\} \quad \text{a}$$

$$T_n = -\Delta t/\tau_n \quad \text{b}$$

$$S_{nk} = X_{k-1} + \exp(T_n) \cdot S_{n(k-1)} \quad \text{c}$$

where Δt: the sampling time interval;
k: a subscript representing a k-th point of time in a sampling time series;
$Y_k$: an X-ray detection signal taken at the k-th sampling time;
$X_k$: a corrected X-ray detection signal with a lag-behind part removed from the signal $Y_k$;
$X_{k-1}$: a signal $X_k$ taken at a preceding point of time;
$S_{n(k-1)}$: an $S_{nk}$ at a preceding point of time;
exp: an exponential function;
N: the number of exponential functions with different time constants forming the impulse response;
n: a subscript representing one of the exponential functions forming the impulse response;
$\alpha_n$: an intensity of exponential function n; and
$\tau_n$: an attenuation time constant of exponential function n.

In the above recursive computation, coefficients of the impulse response of the FPD, N, $\alpha_n$ and $\tau_n$, are determined in advance. With the coefficients fixed, X-ray detection signal $Y_k$ is applied to equations a-c, thereby obtaining a lag-free X-ray detection signal $X_k$.

In the technique described above, where there is only one attenuation time constant, only one exponential function forming the impulse response is required. However, where there are a plurality of different attenuation time constants, the same number of exponential functions forming the impulse response are required. Where a plurality of exponential functions are used, the correcting computation for removing a lag-behind part will take time. It is also time-consuming to determine a plurality of attenuation time constants and intensities.

Inventors herein have considered the possibility of determining one attenuation time constant where there are a plurality of different attenuation time constants. That is, if one exponential function can be determined, a correcting computation may be performed by using only the impulse response formed of the one exponential function determined. FIG. 9 is a view showing a state of radiation incidence. FIG. 10 is a view showing a time delay corresponding to the radiation incidence of FIG. 9.

As shown in FIG. 9, when an incidence of X rays takes place, lag-behind parts shown in hatching in FIG. 10 add to a normal signal corresponding to an incident dose. This results in a radiation detection signal $Y_k$ shown in thick lines in FIG. 10. The above technique may be used to remove the lag-behind parts, i.e. the hatched portions in FIG. 10, to obtain a proper signal.

Regarding the time delay resulting from the impulse response shown in the hatched portions in FIG. 10, where there are a plurality of different attenuation time constants as noted above, there are the same number of exponential functions forming the impulse response. The time delay shown in the hatched portions in FIG. 10 includes also a portion, though gradually attenuating, remaining after the X-ray emission. Inventors herein have noted that the lag-behind part remaining after the X-ray emission is variable with the attenuation time constant, intensity and X-ray radiation time, and attained findings that the impulse response may be determined to have a single exponential function based on an attenuation time constant, intensity or X-ray radiation time having a value for attenuating the lag-behind part to noise level. The "noise level" in this specification refers to a signal strength zero or more which, preferably, is infinitely close to zero. Thus, when the operator determines that a signal is negligible in an X-ray non-emission state, the signal is considered to be at noise level.

Based on the above findings, this invention provides a radiographic apparatus having a radiation emitting device for emitting radiation toward an object under examination, a radiation detecting device for detecting radiation transmitted through the object under examination, and a signal sampling device for taking radiation detection signals from the radiation detecting device at predetermined sampling time intervals, for obtaining radiographic images based on the radiation detection signals outputted from the radiation detecting device at the predetermined sampling time intervals as radiation is emitted to the object under examination, the apparatus comprising:

a time lag removing device for removing lag-behind parts from the radiation detection signals by a recursive computation, on an assumption that a lag-behind part included in each of the radiation detection signals taken at the predetermined sampling time intervals is due to an impulse response formed of a plurality of exponential functions with different attenuation time constants; and an impulse response determining device for determining an impulse response having a single exponential function from the impulse response formed of a plurality of exponential functions, based on an attenuation time constant having a value for attenuating each of the radiation detection signals to a noise level in a radiation non-emission state following a radiation emission state;

wherein the time lag removing device is arranged to obtain corrected radiation detection signals by using the impulse response determined by the impulse response determining device and having a single exponential function, and removing the lag-behind parts from the radiation detection signals.

With the radiographic apparatus according to this invention, radiation detection signals are outputted from the radiation detecting device at predetermined sampling time intervals as radiation is emitted from the radiation emitting device to an object under examination. A lag-behind part included in each of the radiation detection signals is regarded as due to an impulse response formed of a plurality of exponential functions with different attenuation time constants. The time lag removing device removes such lag-behind parts by using impulse responses corresponding to doses of radiation. A radiographic image is obtained from corrected radiation detection signals with the lag-behind parts removed.

The impulse response determining device determines an impulse response having a single exponential function from the impulse response formed of a plurality of exponential functions, based on an attenuation time constant having a value for attenuating each of the radiation detection signals to a noise level in a radiation non-emission state following a radiation emission state. The time lag removing device removes the lag-behind parts from the radiation detection signals by a computation using the impulse response determined, thereby obtaining corrected radiation detection signals. Thus, what is necessary is only to determine one exponential function forming the impulse response, thereby realizing a simple determination of a time lag. Since the noise level is a level for allowing the signal to be disregarded even in a radiation non-emission state, the impulse response determined is highly reliable.

To obtain an impulse response with increased reliability, it is preferable that, in the above radiographic apparatus, the impulse response determining device is arranged to determine the impulse response having a single exponential function by using an attenuation time constant having a value for attenuating each of the radiation detection signals to the noise level in the radiation non-emission state following the radiation emission state, within one second of a start of the radiation non-emission state, and an intensity of the radiation.

According to such an apparatus, the impulse response having a single exponential function is determined by using an attenuation time constant for attenuating the signal to the noise level within one second of the start of the non-emission state following the radiation emission state, and a radiation intensity. The impulse response determined in this way has increased reliability. The impulse response has the higher reliability, the shorter time is taken for the attenuation to the noise level.

To obtain an impulse response with increased reliability, it is also preferable that, in the above radiographic apparatus, the impulse response determining device is arranged to determine the impulse response having a single exponential function by using an attenuation time constant having a value in a range of 0.5 seconds to 1.0 second, and an intensity of the radiation having a value for attenuating each of the radiation detection signals to the noise level in the radiation non-emission state following the radiation emission state.

According to such an apparatus, the impulse response having a single exponential function is determined by using an attenuation time constant having a value in a range of 0.5 seconds to 1.0 second, and an intensity of the radiation having a value for attenuating each of the radiation detection signals to the noise level in the radiation non-emission state following the radiation emission state. The impulse response determined in this way has increased reliability. The impulse response has the higher reliability, the shorter time is taken for the attenuation to the noise level. Where the attenuation time constant is fixed, attenuations may take place in the radiation non-emission state as shown in FIG. 11. With the attenuation time constant exceeding 1.0 second, as shown in an alternate long and short dash line (with the attenuation time constant fixed to 2.0 seconds) and a two-dot chain line in FIG. 11, the signal attenuates to the noise level only slowly. Conversely, with the attenuation time constant less than 0.5 seconds, as shown in a broken line (with the attenuation time constant fixed to 0.4 seconds) in FIG. 11, the signal once attenuates to the noise level and then swings by a large extent above the noise level. Thus, when an intensity is determined with the attenuation time constant fixed, a preferred range is from 0.5 seconds to 1.0 second.

To attenuate the radiation detection signals properly to the noise level, it is preferable that, in the above radiographic apparatus, the radiation emitting device is arranged to emit the radiation to provide a radiation emitting time in a range of five seconds to 15 seconds in the radiation emission state preceding the radiation non-emission state.

According to such an apparatus, the radiation detection signals may be attenuated properly to the noise level by causing the radiation emitting device to emit the radiation to provide a radiation emitting time in a range of five seconds to 15 seconds in the radiation emission state preceding the radiation non-emission state. As noted hereinbefore, Inventors have attained findings that the time lag varies also with radiation emitting time. As a result of adjusting the emission time, it has been found that a radiation emitting time in a range of five seconds to 15 seconds can attenuate the radiation detection signals properly.

In the above radiographic apparatus, it is preferred that the time lag removing device is arranged to perform the recursive computation for removing the lag-behind part from each of the radiation detection signals, based on the following equations A-C:

$$X_k = Y_k - \sum_{n=1}^{N} \{\alpha_n \cdot [1 - \exp(T_n)] \cdot \exp(T_n) \cdot S_{nk}\} \quad \text{A}$$

$$T_n = -\Delta t / \tau_n \quad \text{B}$$

$$S_{nk} = X_{k-1} + \exp(T_n) \cdot S_{n(k-1)} \quad \text{C}$$

where $\Delta t$: the sampling time interval;

k: a subscript representing a k-th point of time in a sampling time series;

$Y_k$: an X-ray detection signal taken at the k-th sampling time;

$X_k$: a corrected X-ray detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n; and to remove the lag-behind part by using the impulse response determined by the impulse response determining device and having a single exponential function.

Where the recursive computation for removing the lag-behind part from each of the radiation detection signals is based on equations A-C, the corrected, lag-free X-ray detection signal $X_k$ may be derived promptly from equations A-C constituting a compact recurrence formula.

In the radiographic apparatus, one example of the radiation detecting device is a flat panel X-ray detector having numerous X-ray detecting elements arranged longitudinally and transversely on an X-ray detecting surface.

The radiographic apparatus according to this invention may be a medical apparatus, and an apparatus for industrial use as well. An example of medical apparatus is a fluoroscopic apparatus. Another example of medical apparatus is an X-ray CT apparatus. An example of apparatus for industrial use is a nondestructive inspecting apparatus.

In another aspect of the invention, a radiation detection signal processing method is provided for taking, at predetermined sampling time intervals, radiation detection signals generated by irradiating an object under examination, and performing a signal processing to obtain radiographic images based on the radiation detection signals outputted at the predetermined sampling time intervals, the method comprising the steps of:

removing lag-behind parts from the radiation detection signals by a recursive computation, on an assumption that a lag-behind part included in each of the radiation detection signals taken at the predetermined sampling time intervals is due to an impulse response formed of a plurality of exponential functions with different attenuation time constants;

determining, prior to the above removing step, an impulse response having a single exponential function from the impulse response formed of a plurality of exponential functions, based on an attenuation time constant having a value for attenuating each of the radiation detection signals to a noise level in a radiation non-emission state following a radiation emission state; and obtaining corrected radiation detection signals by using the impulse response determined in the above determining step and removing the lag-behind parts from the radiation detection signals.

This radiation detection signal processing method allows the radiographic apparatus according to the invention to be implemented in an advantageous manner.

To obtain an impulse response with increased reliability, it is preferable that, in the above radiation detection signal processing method, the determining step is executed to determine the impulse response having a single exponential function by using an attenuation time constant having a value for attenuating each of the radiation detection signals to the noise level in the radiation non-emission state following the radiation emission state, within one second of a start of the radiation non-emission state, and an intensity of the radiation.

Such a method can advantageously implement the radiographic apparatus in which the impulse response determining device is arranged to determine the impulse response having a single exponential function by using an attenuation time constant having a value for attenuating each of the radiation detection signals to the noise level in the radiation non-emission state following the radiation emission state, within one second of a start of the radiation non-emission state, and an intensity of the radiation.

To obtain an impulse response with increased reliability, it is also preferable that, in the above radiation detection signal processing method, the determining step is executed to determine the impulse response having a single exponential function by using an attenuation time constant having a value in a range of 0.5 seconds to 1.0 second, and an intensity of the radiation having a value for attenuating each of the radiation detection signals to the noise level in the radiation non-emission state following the radiation emission state.

Such a method can advantageously implement the radiographic apparatus in which the impulse response determining device is arranged to determine the impulse response having a single exponential function by using an attenuation time constant having a value in a range of 0.5 seconds to 1.0 second, and an intensity of the radiation having a value for attenuating each of the radiation detection signals to the noise level in the radiation non-emission state following the radiation emission state.

To attenuate the radiation detection signals properly to the noise level, it is preferable that, in the above radiation detection signal processing method, the radiation is emitted to provide a radiation emitting time in a range of five seconds to 15 seconds in the radiation emission state preceding the radiation non-emission state.

Such a method can advantageously implement the radiographic apparatus in which the radiation emitting device is arranged to emit the radiation to provide a radiation emitting time in a range of five seconds to 15 seconds in the radiation emission state preceding the radiation non-emission state.

In the above radiation detection signal processing method, it is preferred that the recursive computation for removing the lag-behind part from each of the radiation detection signals is performed based on the following equations A-C:

$$X_k = Y_k - \Sigma_{n=1}^{N}\{\alpha_n \cdot [1-\exp(T_n)] \cdot \exp(T_n) \cdot S_{nk}\} \quad A$$

$$T_n = -\Delta t / \tau_n \quad B$$

$$S_{nk} = X_{k-1} + \exp(T_n) \cdot S_{n(k-1)} \quad C$$

where $\Delta t$: the sampling time interval;

k: a subscript representing a k-th point of time in a sampling time series;

$Y_k$: an X-ray detection signal taken at the k-th sampling time;

$X_k$: a corrected X-ray detection signal with a lag-behind part removed from the signal $Y_k$;

$X_{k-1}$: a signal $X_k$ taken at a preceding point of time;

$S_{n(k-1)}$ an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n; and the lag-behind part is removed by using the impulse response determined in the determining step and having a single exponential function.

Where the recursive computation for removing the lag-behind part from each of the radiation detection signals is based on equations A-C, the radiographic apparatus which performs the recursive computation based on equations A-C may be implemented in an advantageous manner.

In one example of the radiation detection signal processing method, a detection signal processing including the determining step is performed by using a phantom as an object, in order to determine the impulse response having a single exponential function, and a detection signal processing including the removing step and the obtaining step is performed by using the impulse response determined and the object under examination.

In another example of the radiation detection signal processing method, the determining step includes:

repeating a series of operations for provisionally setting an attenuation time constant and an intensity constituting the impulse response, and determining whether, with the set impulse response, an attenuation to the noise level has occurred within a predetermined time, until the impulse response is found appropriate for causing an attenuation to the noise level within the predetermined time; and establishing the impulse response as valid when the impulse response is found appropriate.

In the radiation detection signal processing method, the determining step may be executed by a central processing unit, or may be executed manually.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

Preferred embodiments of this invention will be described in detail hereinafter with reference to the drawings.

First Embodiment

Figure 1:
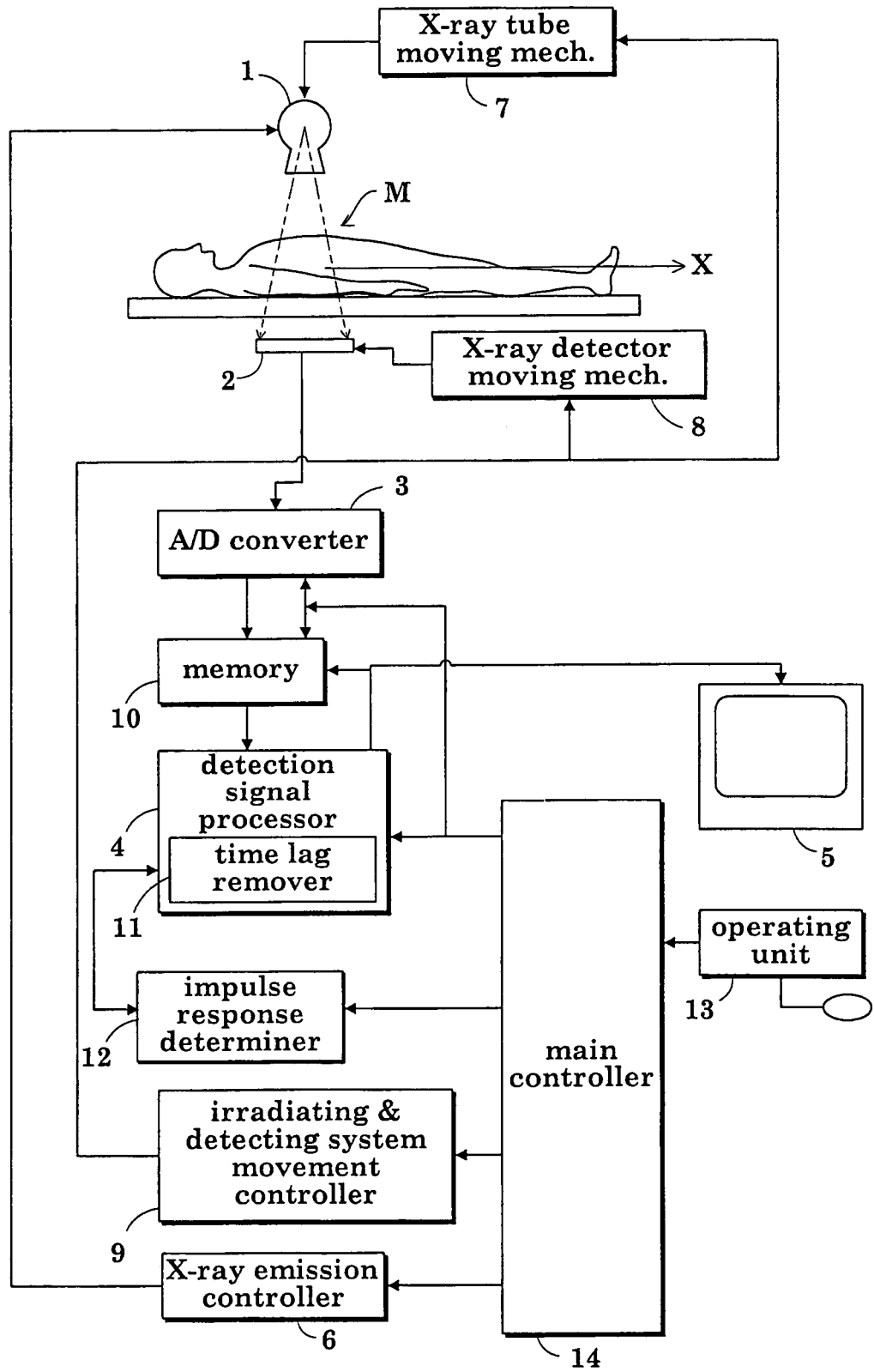
FIG. 1 is a block diagram showing an overall construction of a fluoroscopic apparatus according to the invention.

FIG. 1 is a block diagram showing an overall construction of a fluoroscopic apparatus in a first embodiment of this invention.

As shown in FIG. 1, the fluoroscopic apparatus includes an X-ray tube (radiation emitting device) 1 for emitting X rays toward a patient M, an FPD 2 (radiation detecting device) for detecting X rays transmitted through the patient M, an analog-to-digital converter 3 (signal sampling device) for digitizing X-ray detection signals (radiation detection signals) taken from the FPD (flat panel X-ray detector) 2 at predetermined sampling time intervals $\Delta t$, a detection signal processor 4 for creating X-ray images based on X-ray detection signals outputted from the analog-to-digital converter 3, and an image monitor 5 for displaying the X-ray images created by the detection signal processor 4. That is, the apparatus is constructed to acquire X-ray images from the X-ray detection signals taken from the FPD 2 by the analog-to-digital converter 3 as the patient M is irradiated with X rays, and display the acquired X-ray images on the screen of the image monitor 5. Each component of this apparatus will particularly be described hereinafter.

The X-ray tube 1 and FPD 2 are opposed to each other across the patient M. In time of X-ray radiography, the X-ray tube 1 is controlled by an X-ray emission controller 6 to emit X rays in the form of a cone beam to the patient M. At the same time, penetration X-ray images of the patient M produced by the X-ray emission are projected to an X-ray detecting surface of FPD 2.

The X-ray tube 1 and FPD 2 are movable back and forth along the patient M by an X-ray tube moving mechanism 7 and an X-ray detector moving mechanism 8, respectively. In moving the X-ray tube 1 and FPD 2, the X-ray tube moving mechanism 7 and X-ray detector moving mechanism 8 are controlled by an irradiating and detecting system movement controller 9 to move the X-ray tube 1 and FPD 2 together as opposed to each other, with the center of emission of X rays constantly in agreement with the center of the X-ray detecting surface of FPD 2. Of course, movement of the X-ray tube 1 and FPD 2 results in variations in the position of the patient M irradiated with X rays, hence movement of a radiographed site.

Figure 2:
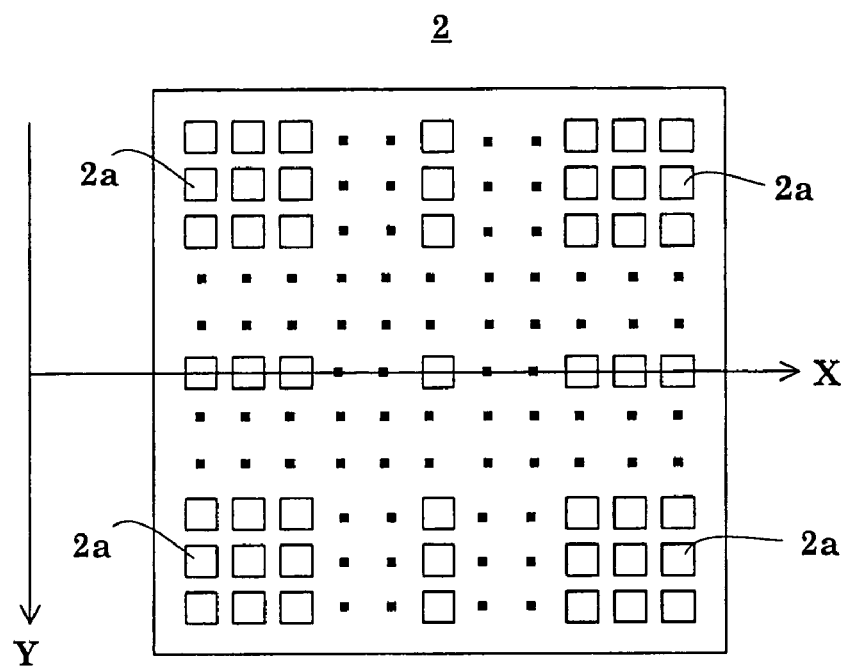
FIG. 2 is a plan view of an FPD used in the fluoroscopic apparatus.

As shown in FIG. 2, the FPD 2 has numerous X-ray detecting elements 2a arranged longitudinally and transversely along the direction X of the body axis of patient M and the direction Y perpendicular to the body axis, on the X-ray detecting surface to which penetration X-ray images from the patient M are projected. For example, X-ray detecting elements 2a are arranged to form a matrix of 1536 by 1536 on the X-ray detecting surface about 30 cm long and 30 cm wide. Each X-ray detecting element 2a of FPD 2 corresponds to one pixel in an X-ray image created by the detection signal processor 4. Based on the X-ray detection signals taken from the FPD 2, the detection signal processor 4 creates an X-ray image corresponding to a penetration X-ray image projected to the X-ray detecting surface.

The analog-to-digital converter 3 continually takes X-ray detection signals for each X-ray image at sampling time intervals $\Delta t$, and stores the X-ray detection signals for X-ray image creation in a memory 10 disposed downstream of the converter 3. An operation for sampling (extracting) the X-ray detection signals is started before X-ray irradiation.

Figure 3:
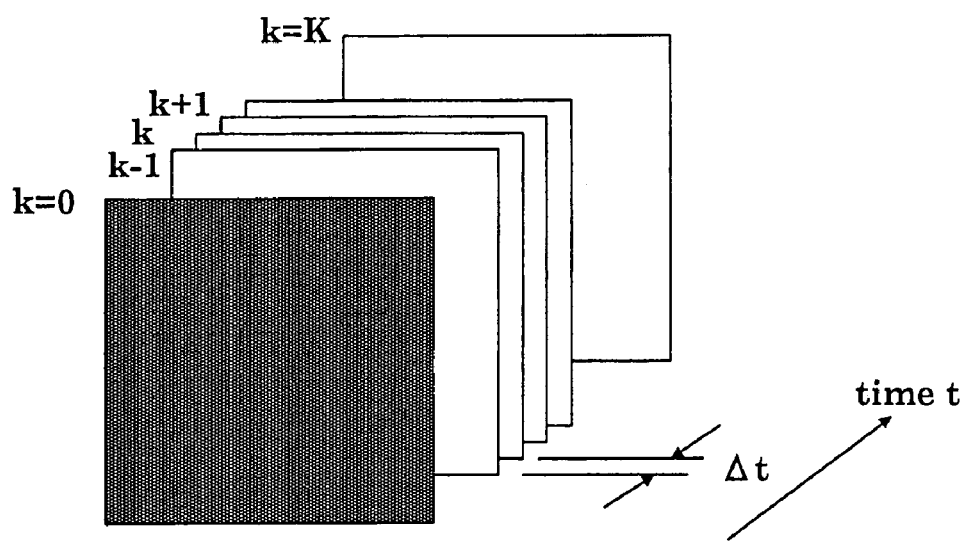
FIG. 3 is a schematic view showing a state of sampling X-ray detection signals during X-ray radiography by the fluoroscopic apparatus.

That is, as shown in FIG. 3, all X-ray detection signals for a penetration X-ray image are collected at each period between the sampling intervals $\Delta t$, and are successively stored in the memory 10. The sampling of X-ray detection signals by the analog-to-digital converter 3 before an emission of X rays may be started manually by the operator or automatically as interlocked with a command for X-ray emission.

As shown in FIG. 1, the fluoroscopic apparatus in the first embodiment includes a time lag remover 11 for computing corrected radiation detection signals free from time lags. A time lag is removed from each X-ray detection signal by a recursive computation based on an assumption that a lag-behind part included in each of the X-ray detection signals taken at the sampling time intervals from the FPD 2 is due to an impulse response formed of a plurality of exponential functions with different attenuation time constants. The apparatus further includes an impulse response determiner 12 for determining an impulse response having a single exponential function from impulse responses having a plurality of exponential functions, based on an attenuation time constant having a value for attenuating to a noise level of an X-ray detection signal in an X-ray non-emission state following an X-ray emission state.

Figure 10:
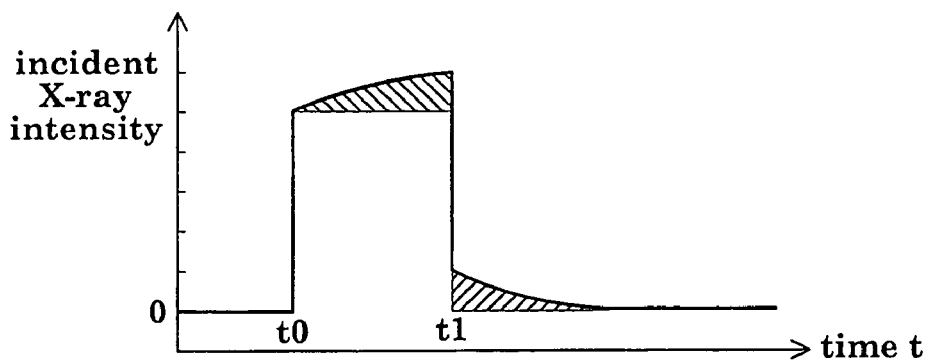
FIG. 10 is a view showing time lags corresponding to the radiation incidence of FIG. 9.
Figure 11:
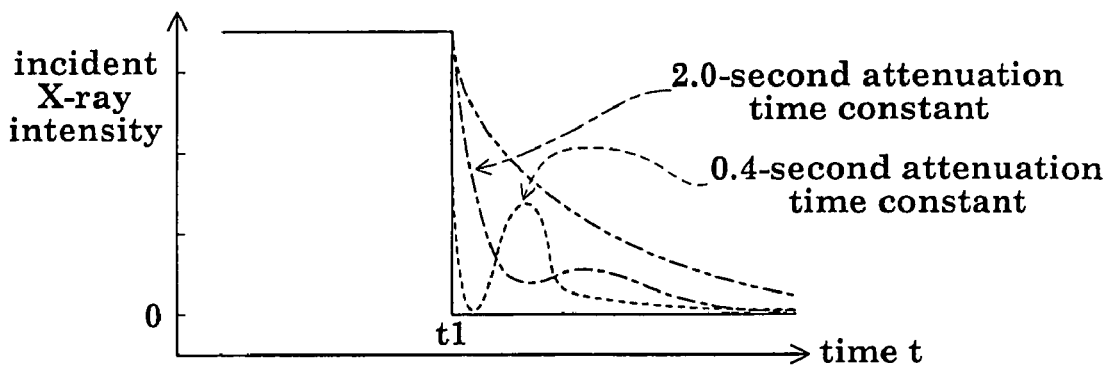
FIG. 11 is a view showing a detection signal in time of transition from an emission state to a non-emission state with values of attenuation time constants fixed.

With the FPD 2, an X-ray detection signal generated at each point of time, as shown in FIG. 10, includes signals corresponding to preceding X-ray emissions and remaining as a lag-behind part (hatched part). The time lag remover 11 removes this lag-behind part to produce a corrected, lag-free X-ray detection signal. Based on such lag-free X-ray detection signals, the detection signal processor 4 creates an X-ray image corresponding to a penetration X-ray image projected to the X-ray detecting surface.

Specifically, the time lag remover 11 performs a recursive computation for removing a lag-behind part from each X-ray detection signal by using the following equations A-C:

$$X_k = Y_k - \Sigma_{n=1}^{N}\{\alpha_n \cdot [1-\exp(T_n)] \cdot \exp(T_n) \cdot S_{nk}\} \quad\quad A$$

$$T_n = -\Delta t / \tau_n \quad\quad B$$

$$S_{nk} = X_{k-1} + \exp(T_n) \cdot S_{n(k-1)} \quad\quad C$$

where $\Delta t$: the sampling time interval;
k: a subscript representing a k-th point of time in a sampling time series;
$Y_k$: an X-ray detection signal taken at the k-th sampling time;
$X^k$: a corrected X-ray detection signal with a lag-behind part removed from the signal $Y_k$;
$X^{k-1}$: a signal $X_k$ taken at a preceding point of time;
$S_{n(k-1)}$: an $S_{nk}$ at a preceding point of time;
exp: an exponential function;
N: the number of exponential functions with different time constants forming the impulse response;
n: a subscript representing one of the exponential functions forming the impulse response;
$\alpha_n$: an intensity of exponential function n; and
$\tau_n$: an attenuation time constant of exponential function n.

The second term in equation A "$\Sigma_{n=1}^{N}\{\alpha_n \cdot [1-\exp(T_n)] \cdot \exp(T_n) \cdot S_{nk}\}$" corresponds to the lag-behind part. Thus, the apparatus in the first embodiment derives the corrected, lag-free X-ray detection signal $X_k$ promptly from equations A-C constituting a compact recurrence formula.

To make the recurrence formula still more compact, the impulse response determiner 12 of the apparatus in the first embodiment determines an impulse response having a single exponential function. A procedure for determining an impulse response will be described hereinafter with reference to the flow chart shown in FIG. 4.

In the first embodiment, the analog-to-digital converter 3, detection signal processor 4, X-ray emission controller 6, irradiating and detecting system movement controller 9, time lag remover 11 and impulse response determiner 12 are operable on instructions and data inputted from an operating unit 12 or on various commands outputted from a main controller 13 with progress of X-ray radiography.

Next, an operation for performing X-ray radiography with the apparatus in the first embodiment will particularly be described with reference to the drawings.

Figure 4:
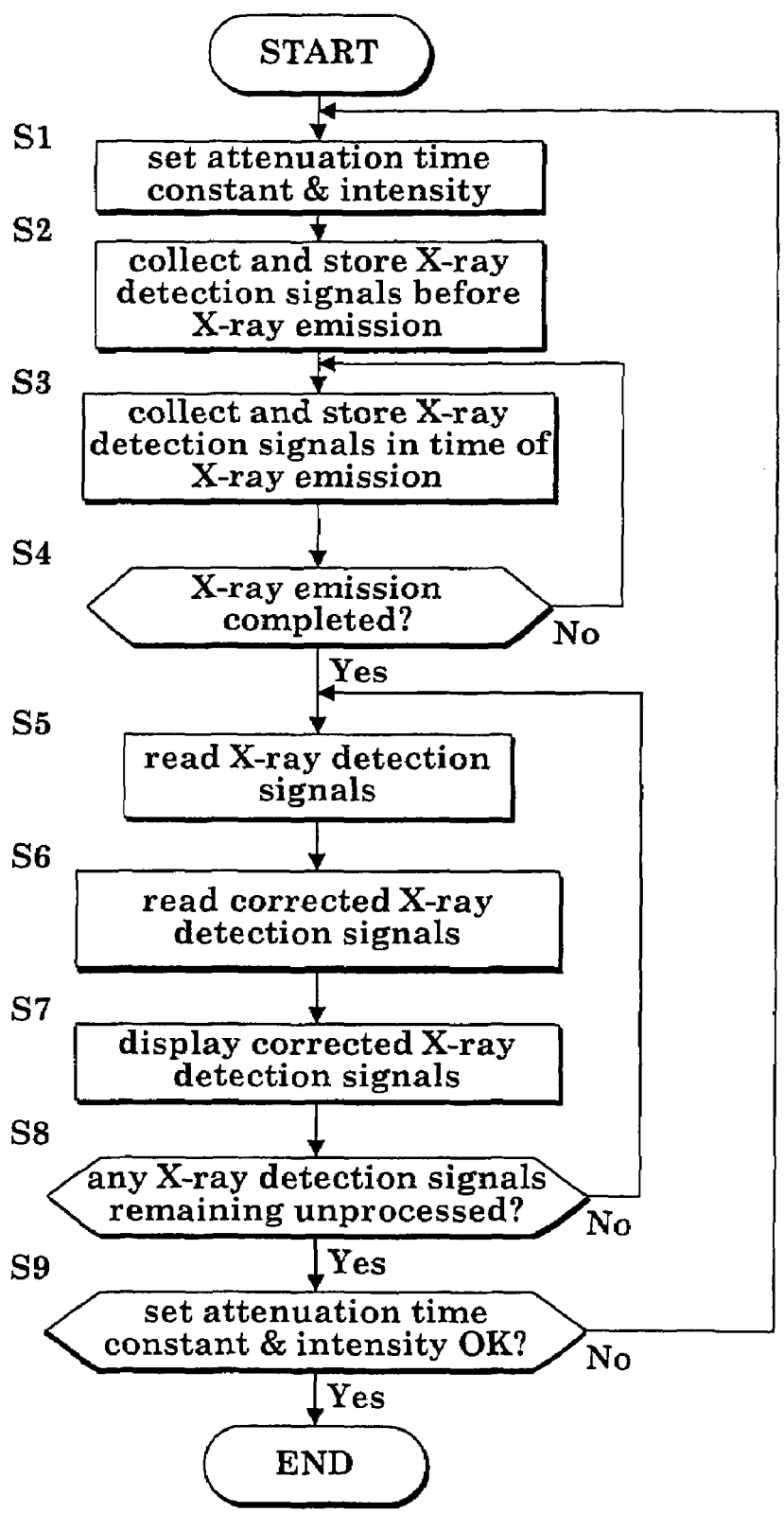
FIG. 4 is a flow chart showing a procedure, up to determination of an impulse response, of an X-ray detection signal processing method in a first embodiment.
Figure 5:
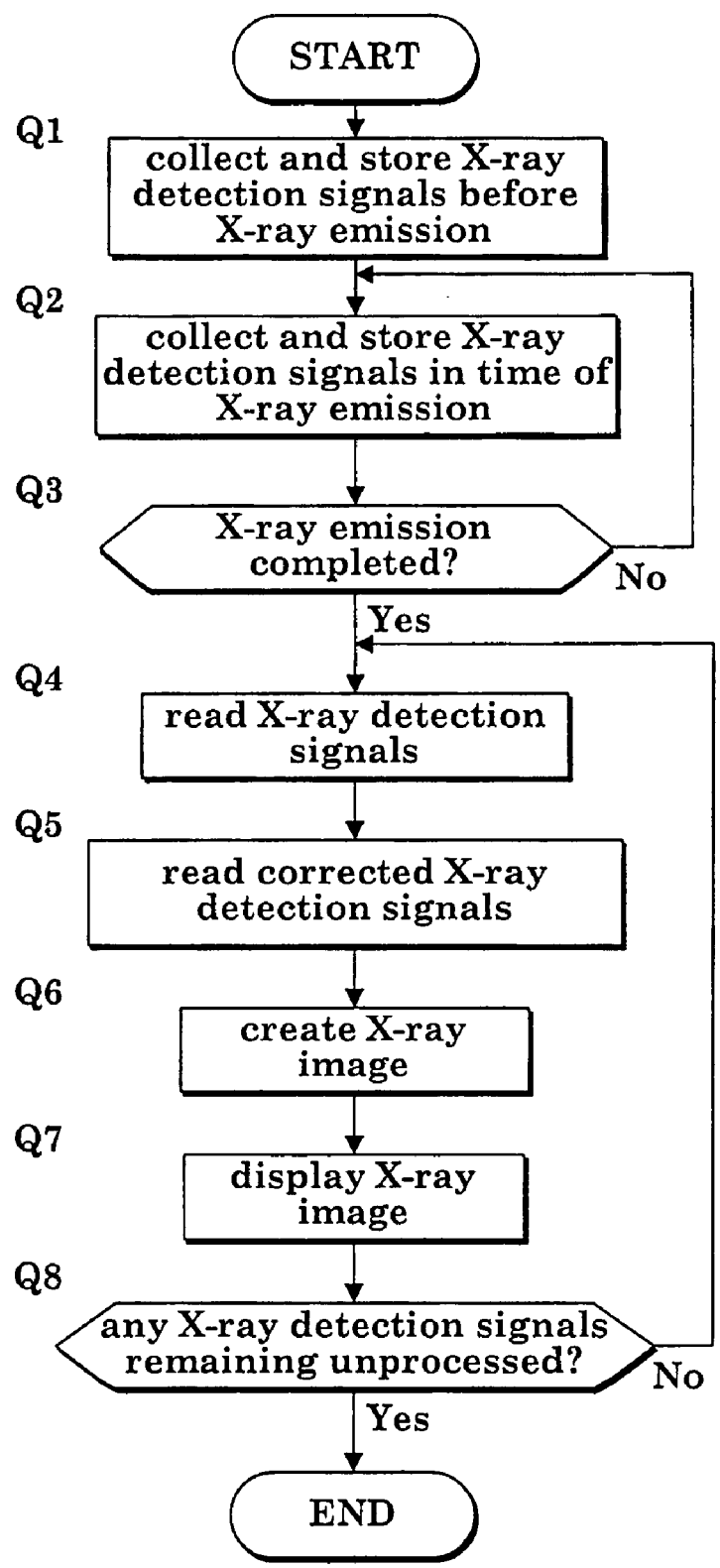
FIG. 5 is a flow chart showing a procedure, after determination of the impulse response, of the X-ray detection signal processing method in the first and a second embodiments.
Figure 7:
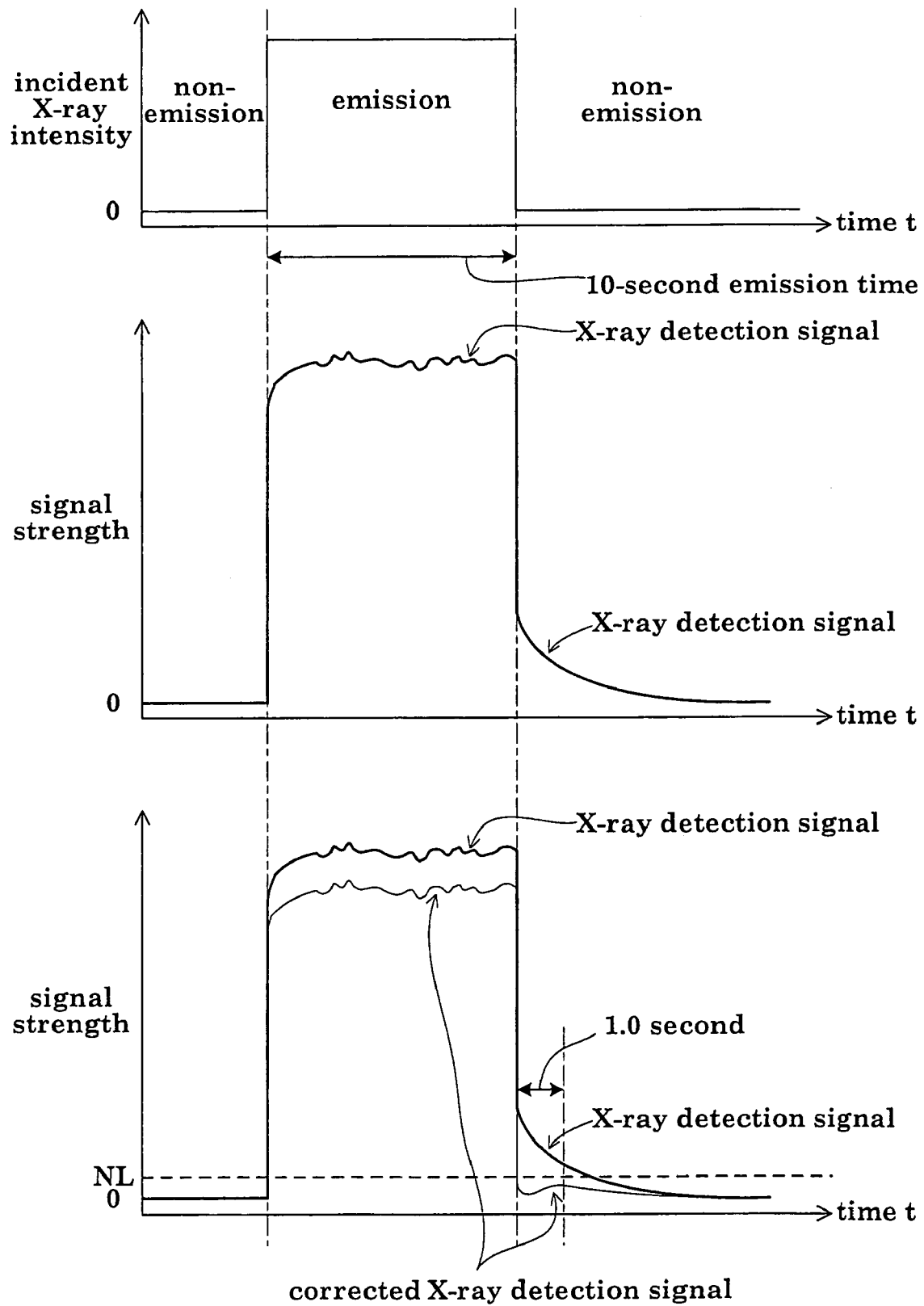
FIG. 7 is a view showing a state of X-ray incidence in the first embodiment.

FIGS. 4 and 5 are flow charts showing a procedure of X-ray radiography in this embodiment. FIG. 4 is a flow chart showing a procedure, up to determination of an impulse response, of an X-ray detection signal processing method in the first embodiment. FIG. 5 is a flow chart showing a procedure, after determination of the impulse response, of the X-ray detection signal processing method. FIG. 7 is a view showing a state of radiation incidence in the first embodiment, in which the top figure is a time chart of X-ray emission, the middle figure shows data at each period between the sampling time intervals of an X-ray detection signal obtained from the X-ray emission, and the bottom figure shows data at each period between the sampling time intervals of the X-ray detection signal and corrected X-ray detection signal.

In the flow chart (steps S1-S9) shown in FIG. 4, detection signals are processed by using a stationary object (e.g. a copper phantom) serving as the patient M.

[Step S1] The operator predicts that the corrected X-ray correcting detection signal $X_k$ attenuates to a noise level NL (top in FIG. 7) within one second of the start of an X-ray non-emission state, and provisionally sets attenuation time constant $\tau_n$ and intensity $\alpha_n$.

[Step S2] The analog-to-digital converter 3 starts taking X-ray detection signals $Y_k$ for one X-ray image from the FPD 2 at each period between the sampling time intervals $\Delta t$ (=1/30 second) before X-ray emission. The X-ray detection signals taken are stored in the memory 10.

Step S2 to step S6 are the same as step Q1 to step Q5 in FIG. 5 executed after determining an impulse response.

[Step S3] In parallel with a continuous or intermittent X-ray emission to the patient M initiated by the operator, the analog-to-digital converter 3 continues taking X-ray detection signals $Y_k$ for one X-ray image at each period between the sampling time intervals $\Delta t$ and storing the signals in the memory 10.

Inventors have attained findings that the time lag varies also with X-ray emission time. For the corrected X-ray detection signal $X_k$ to attenuate properly to noise level, the X-ray emission time, preferably, is in a range of five to 15 seconds, and more desirably, 10 seconds. In the first embodiment, the emission time is set to 10 seconds as shown in the top of FIG. 7.

[Step S4] When the X-ray emission is completed, the operation proceeds to step S5. When the X-ray emission is uncompleted, the operation returns to step S3.

[Step S5] X-ray detection signals $Y_k$ for one X-ray image collected in one sampling sequence are read from the memory 10.

[Step S6] The time lag remover 11 performs the recursive computation based on the equations A-C, and derives corrected X-ray detection signals $X_k$, i.e. pixel values, with lag-behind parts removed from the respective X-ray detection signals $Y_k$.

[Step S7] The corrected X-ray detection signals $X_k$ for one sampling sequence (for one X-ray image) are displayed on the image monitor 5 (see the bottom view in FIG. 7).

[Step S8] When unprocessed X-ray detection signals $Y_k$ remain in the memory 10, the operation returns to step S5. When no unprocessed X-ray detection signals $Y_k$ remain, the X-ray radiography is ended.

In the first embodiment, the time lag remover 11 computes the corrected X-ray detection signals $X_k$ corresponding to the X-ray detection signals $Y_k$ for one X-ray image, and the image display monitor 5 displays the X-ray detection signals $Y_k$, both at sampling time intervals $\Delta t$ (=1/30 second). The X-ray detection signal $Y_k$ obtained at each period between the sampling time intervals $\Delta t$ provides data as shown at the bottom of FIG. 7.

[Step S9] On the other hand, the impulse response determiner 12 determines whether, in an X-ray non-emission state following an emission state, the corrected X-ray detection signal $X_k$ has attenuated to the noise level NL shown at the bottom of FIG. 7. In the first embodiment, the impulse response determiner 12 determines whether the corrected X-ray detection signal $X_k$ reached the noise level NL within one second of the start of the non-emission state.

When the time for reaching the noise level NL exceeds one second from the start, or when the noise level NL is reached within one second but the noise level NL is exceeded thereafter, the impulse response determiner 12 determines that the impulse response with the set attenuation time constant $\tau_n$ and intensity $\alpha_n$ is inappropriate. Conversely, when the time for reaching the noise level NL is within one second and the signal thereafter remains below the noise level NL, the impulse response determiner 12 determines that the impulse response with the set attenuation time constant $\tau_n$ and intensity $\alpha_n$ is appropriate.

When the impulse response with the attenuation time constant $\tau_n$ and intensity $\alpha_n$ set in step S1 is found inappropriate, the procedure returns to step S1 for the operator to set different attenuation time constant $\tau_n$ and intensity $\alpha_n$. When the impulse response is found appropriate, the impulse response determiner 12 establishes this impulse response as valid. Since the set attenuation time constant $\tau_n$ and intensity $\alpha_n$ are singular, only one impulse response is established.

While the impulse response determiner 12 determines an impulse response in the first embodiment, a different component (e.g. the main controller 14) may have the function for determining an impulse response. Further, while the impulse response determiner 12 determines whether an impulse response is appropriate or not, a component other than the impulse response determiner 12 may perform this function separately from the determination of the impulse response by the impulse response determiner 12. That is, a CPU (central processing unit) represented by the impulse response determiner 12 or main controller 14 may determine an impulse response and determine whether the impulse response is appropriate or not. Further, the operator may observe what is displayed on the image display monitor 5, and determine based on the observation whether the impulse response is appropriate or not.

The "noise level" in this specification refers to a signal strength zero or more which, preferably, is infinitely close to zero. Thus, when the operator determines a signal in time of non-emission of X rays to be negligible, the signal is considered to be at the noise level NL. When the impulse response determiner 12 determines whether an impulse response is appropriate, the operator sets beforehand the noise level NL at which the signal is negligible even in the non-emission state, and appropriateness of the impulse response may be determined according to the set noise level NL. When appropriateness of the impulse response is determined from a result displayed on the image display monitor 5, the operator may observe the displayed result and determine the impulse response to be appropriate if the signal is negligible even in the non-emission state.

Next, the procedure shown in the flow chart of FIG. 5 is performed using the impulse response determined in FIG. 4. In the flow chart (steps Q1-Q8) of FIG. 5, detection signals are processed using the patient M who is the actual object of radiation detection.

[Step Q1] Same as step S2 in FIG. 4.
[Step Q2] Same as step S3 in FIG. 4.
[Step Q3] Same as step S4 in FIG. 4.
[Step Q4] Same as step S5 in FIG. 4.
[Step Q5] Same as step S6 in FIG. 4. However, the recursive computation is performed at this time by using the single impulse response determined in FIG. 4.

[Step Q6] The detection signal processor 4 creates an X-ray image based on the corrected X-ray detection signals Xk for one sampling sequence (for one X-ray image).

[Step Q7] The X-ray image created is displayed on the image monitor 5.

[Step Q8] When unprocessed X-ray detection signals $Y_k$ remain in the memory 10, the operation returns to step Q4. When no unprocessed X-ray detection signals $Y_k$ remain, the X-ray radiography is ended.

In the first embodiment, the time lag remover 11 computes the corrected X-ray detection signals $X_k$ corresponding to the X-ray detection signals $Y_k$ for one X-ray image, and the detection signal processor 4 creates an X-ray image, both at sampling time intervals $\Delta t$ (=1/30 second). That is, the apparatus is constructed also for creating X-ray images one after another at a rate of about 30 images per second, and displaying the created X-ray images continuously. It is thus possible to perform a dynamic display of X-ray images.

Next, the process of recursive computation carried out in step S6 in FIG. 4 and step Q5 in FIG. 5 by the time lag remover 11 will be described with reference to FIG. 6.

Figure 6:
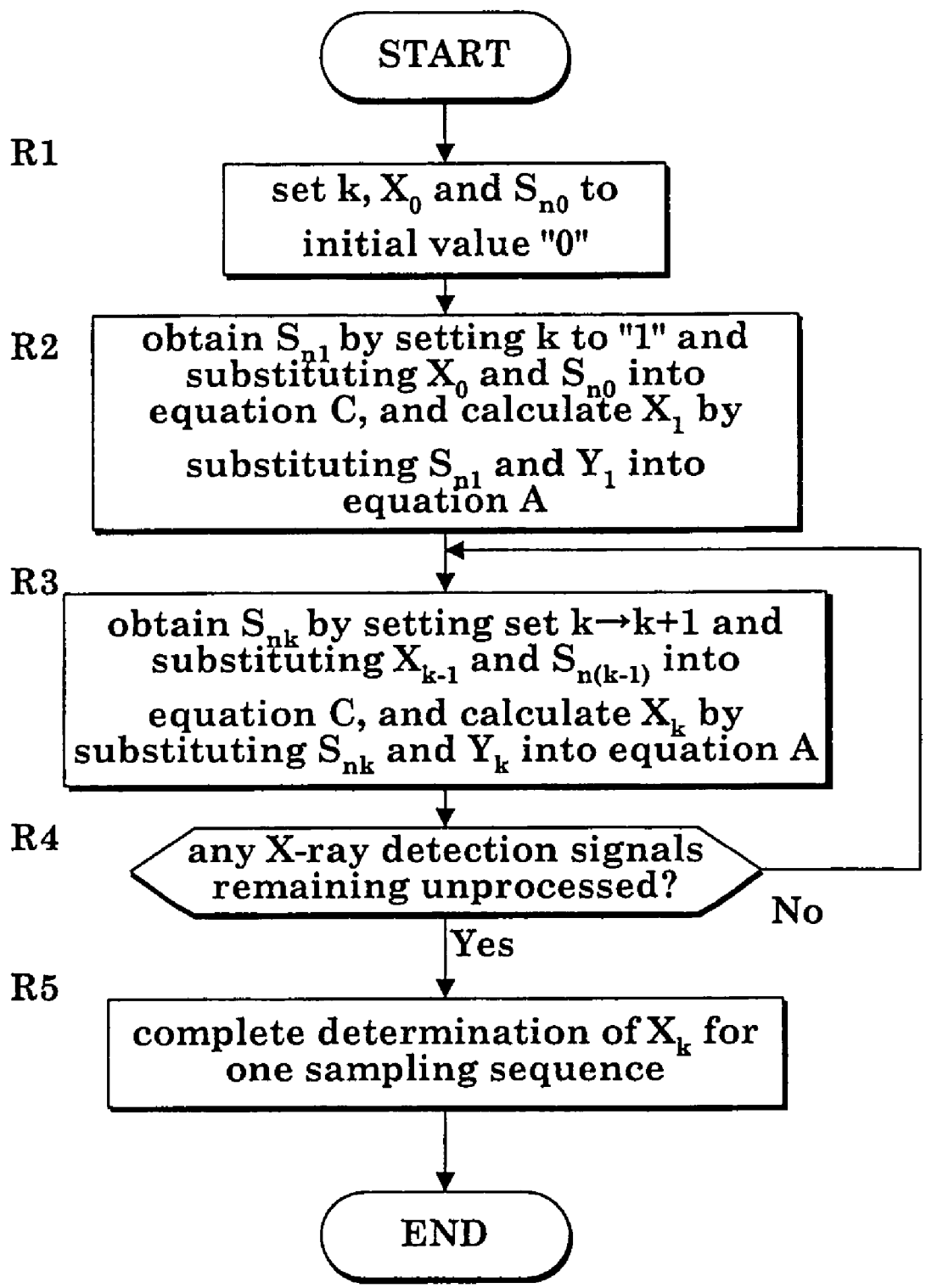
FIG. 6 is a flow chart showing a recursive computation process for time lag removal in the X-ray detection signal processing method in the first and second embodiments.

FIG. 6 is a flow chart showing a recursive computation process for time lag removal in the radiation detection signal processing method in the first embodiment.

[Step R1] A setting k=0 is made, and $X_0$=0 in equation A and $S_{n0}$=0 in equation C are set as initial values before X-ray emission. $S_{10}$ is set to 0 since the exponential function is single (N=1) both before determination of the impulse response (FIG. 4) and after determination of the impulse response (FIG. 5).

[Step R2] In equations A and C, k=1 is set. That is, $S_{11}$ is derived from equation C, i.e. $S_{n1}=X_0+\exp(T_n)\cdot S_{n0}$. Further, a corrected X-ray detection signal is obtained by substituting $S_{11}$ derived and X-ray detection signal $Y_1$ into equation A.

[Step R3] After incrementing k by 1 (k=k+1) in equations A and C, $X_{k-1}$ of a preceding time is substituted into equation C, thereby obtaining $S_{1k}$. Further, corrected X-ray detection signal $X_k$ is obtained by substituting $S_{1k}$ derived and X-ray detection signal $Y_k$ into equation A.

[Step R4] When there remain unprocessed X-ray detection signals $Y_k$, the operation returns to step R3. When no unprocessed X-ray detection signals $Y_k$ remain, the operation proceeds to the next step R5.

[Step R5] Corrected X-ray detection signals $X_k$ for one sampling sequence (for one X-ray image) are obtained to complete the recursive computation for the one sampling sequence.

According to the fluoroscopic apparatus in the first embodiment, as described above, impulse responses of FDD 2 corresponding to the X-ray doses are used when the time lag remover 11 computes corrected X-ray detection signals by removing a lag-behind part from each X-ray detection signal by the recursive computation. Thus, corrected X-ray detection signals are obtained with high accuracy.

For removing a lag-behind part from each X-ray detection signal by the above computation, the impulse response determiner 12 determines an impulse response having a single (one) exponential function from an impulse response having a plurality of (N) exponential functions, based on attenuation time constant $\tau_n$ having a value for attenuating a corrected X-ray detection signal to the noise level NL in an X-ray non-emission state following an X-ray emission. The lag-behind part is removed by using the impulse response determined, to obtain corrected radiation detection signal $X_k$. Thus, what is necessary is only to determine one exponential function forming the impulse response, thereby realizing a simple determination of a time lag. Since the noise level NL is a level for allowing the signal to be disregarded even in an X-ray non-emission state, the impulse response determined is highly reliable.

In the first embodiment, an impulse response having a single exponential function is determined by using attenuation time constant $\tau_n$ for attenuating the signal to the noise level NL within one second of the start of the non-emission state, and intensity $\alpha_n$. The impulse response determined in this way has increased reliability. The impulse response has the higher reliability, the shorter time is taken for the attenuation to the noise level.

In the first embodiment, each X-ray emission time is 10 seconds. An X-ray detection signal may be attenuated appropriately to the noise level by causing the X-ray tube 1 to emit X rays for a time ranging from five seconds to 15 seconds.

Second Embodiment

A second embodiment of this invention will be described next with reference to the drawings.

Figure 8:
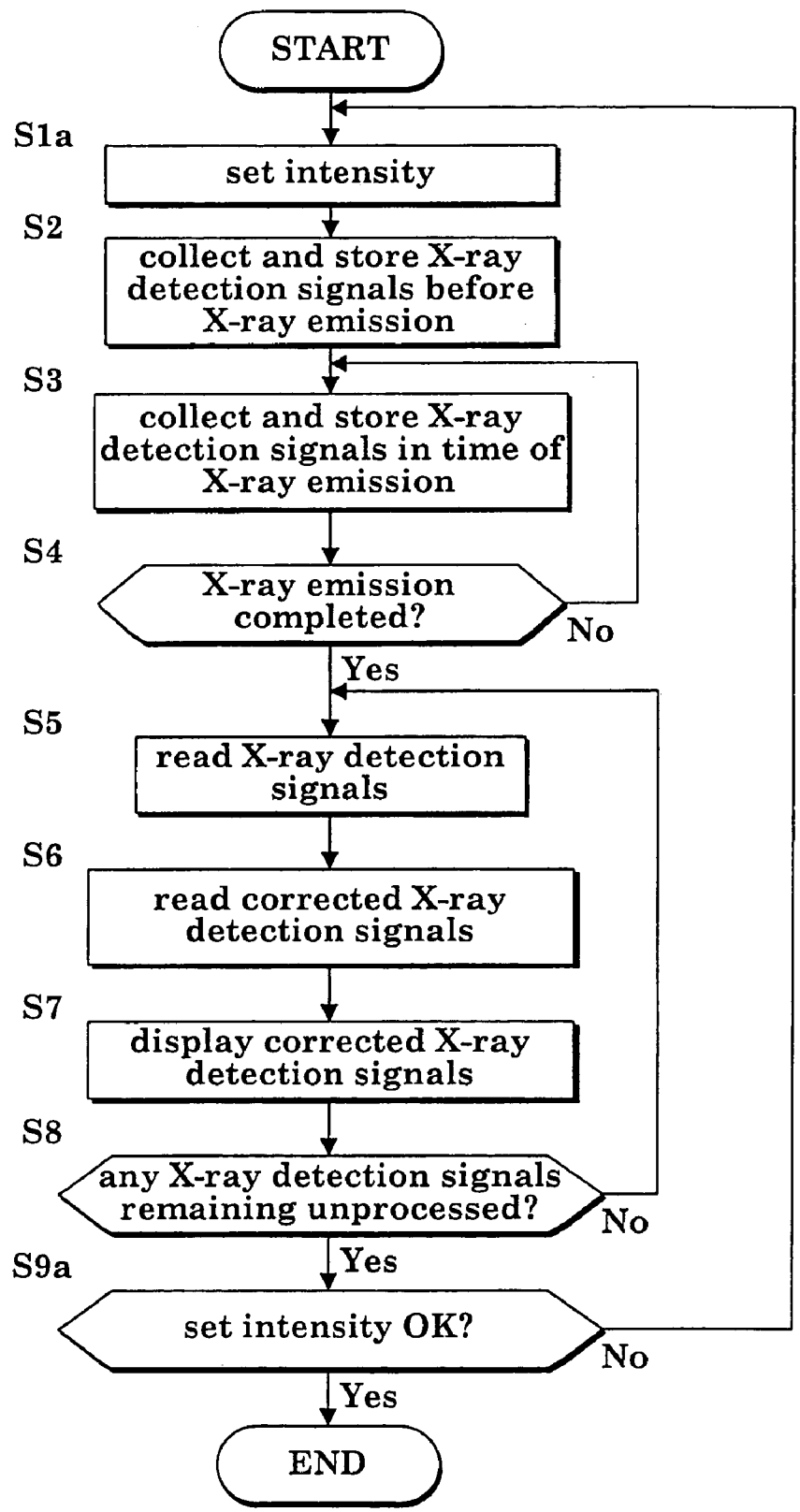
FIG. 8 is a flow chart showing a procedure, up to determination of the impulse response, of an X-ray detection signal processing method in the second embodiment.
Figure 9:
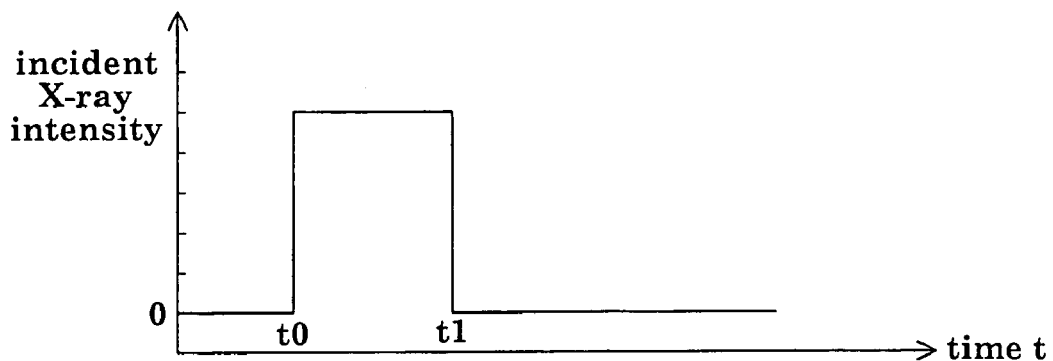
FIG. 9 is a view showing a state of radiation incidence.

FIG. 8 is a flow chart showing a procedure, up to determination of an impulse response, of an X-ray detection signal processing method in the second embodiment. A fluoroscopic apparatus in the second embodiment is the same as the apparatus in the first embodiment except the specific function of the impulse response determiner 12. The procedure, after determination of the impulse response, of the X-ray detection signal processing method and the recursive computation by the time lag remover 11 are the same as in the first embodiment, and will not be described again.

Steps S2 to S8 in the flow chart of the second embodiment shown in FIG. 8 are the same as those in the flow chart of the first embodiment shown in FIG. 4.

[Step S1a] The operator predicts that the signal attenuates to the noise level NL, and provisionally sets intensity $\alpha_n$. At this time, attenuation time constant $\tau_n$ is fixed. Where attenuation time constant $\tau_n$ is fixed and intensity an is determined, attenuation time constant τn, preferably, is in a range of 0.5 seconds to 1.0 second, and more desirably around 0.5 seconds. In the second embodiment, attenuation time constant $\tau_n$ is fixed to 0.5 seconds.

[Step S2] Same as step S2 in FIG. 4.
[Step S3] Same as step S3 in FIG. 4.
[Step S4] Same as step S4 in FIG. 4.
[Step S5] Same as step S5 in FIG. 4.
[Step S6] Same as step S6 in FIG. 4.
[Step S7] Same as step S7 in FIG. 4.
[Step S8] Same as step S8 in FIG. 4.

[Step S9a] The impulse response determiner 12 determines whether, in an X-ray non-emission state following an emission state, the corrected X-ray detection signal $X_k$ has attenuated to the noise level NL. The manner of making this determination is the same as in the first embodiment, and will not described again. However, since attenuation time constant $\tau_n$ is fixed beforehand in the range of 0.5 seconds to 1.0 second, there is no need for the limitation to one second from the start of the non-emission state as in the first embodiment. The attenuation may take place within a predetermined time of the start of the non-emission state. When the signal fails to attenuate to the noise level NL, the impulse response determiner 12 determines that the impulse response with the set intensity $\alpha_n$ is inappropriate. Conversely, when the signal attenuates to the noise level NL, the impulse response determiner 12 determines that the impulse response with the set intensity an is appropriate.

When the impulse response with the intensity $\alpha_n$ set in step S1a is found inappropriate, the procedure returns to step S1a for the operator to set a different intensity an. When the impulse response is found appropriate, the impulse response determiner 12 establishes this impulse response as valid. Since the set intensity $\alpha_n$ is singular, only one impulse response is established.

In the second embodiment, as in the first embodiment, a CPU (central processing unit) represented by the impulse response determiner 12 or main controller 14 may determine an impulse response and determine whether the impulse response is appropriate or not. Further, the operator may observe what is displayed on the image display monitor 5, and determine based on the observation whether the impulse response is appropriate or not.

According to the fluoroscopic apparatus in the second embodiment, as described above, an impulse response having a single exponential function is determined by using attenuation time constant $\tau_n$ ranging from 0.5 seconds to 1.0 second, e.g. 0.5 seconds, and intensity $\alpha_n$ having a value for attenuating the signal to the noise level NL. The impulse response determined in this way has increased reliability.

This invention is not limited to the foregoing embodiments, but may be modified as follows:

(1) The embodiments described above employ an FPD as the radiation detecting device. This invention is applicable also to an apparatus having a radiation detecting device other than an FPD that causes time lags in X-ray detection signals.

(2) While the apparatus in the foregoing embodiments is a fluoroscopic apparatus, this invention is applicable also to an apparatus other than the fluoroscopic apparatus, such as an X-ray CT apparatus.

(3) The apparatus in the foregoing embodiments is designed for medical use. This invention is applicable not only to such medical apparatus but also to an apparatus for industrial use such as a nondestructive inspecting apparatus.

(4) The apparatus in the foregoing embodiments uses X rays as radiation. This invention is applicable also to an apparatus using radiation other than X rays.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus having radiation emitting means for emitting radiation toward an object under examination, radiation detecting means for detecting radiation transmitted through the object under examination, and signal sampling means for taking radiation detection signals from the radiation detecting means at predetermined sampling time intervals, for obtaining radiographic images based on the radiation detection signals outputted from the radiation detecting means at the predetermined sampling time intervals as radiation is emitted to the object under examination, said apparatus comprising:

time lag removing means for removing lag-behind parts from the radiation detection signals by a recursive computation, on an assumption that a lag-behind part included in each of said radiation detection signals taken at the predetermined sampling time intervals is due to an impulse response formed of a plurality of exponential functions with different attenuation time constants; and impulse response determining means for determining an impulse response having a single exponential function from said impulse response formed of a plurality of exponential functions, based on a selected, single, fixed attenuation time constant having a single, fixed value for attenuating each of said radiation detection signals to a noise level in a radiation non-emission state following a radiation emission state;

wherein said time lag removing means is arranged to obtain corrected radiation detection signals by using the impulse response determined by said impulse response determining means and having a single exponential function, and removing the lag-behind parts from the radiation detection signals.

2. A radiographic apparatus as defined in claim 1, wherein said impulse response determining means is arranged to determine said impulse response having a single exponential function by using the selected, single, fixed attenuation time constant having the single, fixed value for attenuating each of said radiation detection signals to said noise level in said radiation non-emission state following said radiation emission state, within one second of a start of said radiation non-emission state, and a selected, single, fixed intensity of the radiation.

3. A radiographic apparatus as defined in claim 1, wherein said impulse response determining means is arranged to determine said impulse response having a single exponential function by using the selected, single, fixed attenuation time constant having the single, fixed value in a range of 0.5 seconds to 1.0 second, and a selected single, fixed intensity of the radiation having a single, fixed value for attenuating each of said radiation detection signals to said noise level in said radiation non-emission state following said radiation emission state.

4. A radiographic apparatus as defined in claim 1, wherein said radiation emitting means is arranged to emit the radiation to provide a radiation emitting time in a range of five seconds to 15 seconds in said radiation emission state preceding said radiation non-emission state.

5. A radiographic apparatus as defined in claim 1, wherein said time lag removing means is arranged to perform the recursive computation for removing the lag-behind part from each of the radiation detection signals, based on the following equations A-C:

$$X_k = Y_k - \Sigma_{n=1}^{N}\{\alpha_n \cdot [1-\exp(T_n)] \cdot \exp(T_n) \cdot S_{nk}\} \qquad A$$

$$T_n = -\Delta t / \Sigma_n \qquad B$$

$$S_{nk} = X_{k-1} + \exp(T_n) \cdot S_{n(k-)} \qquad C$$

where $\Delta t$: the sampling time interval;
k: a subscript representing a k-th point of time in a sampling time series;
$Y_k$: a radiation detection signal taken at the k-th sampling time;
$X_k$: a corrected radiation detection signal with a lag-behind part removed from the signal $Y_k$;
$X_{k-1}$: a signal $X_k$ taken at a preceding point of time;
$S_{n(k-1)}$: an $S_{nk}$ at a preceding point of time;
exp: an exponential function;
N: the number of exponential functions with different time constants forming the impulse response;
n: a subscript representing one of the exponential functions forming the impulse response;
$\alpha_n$: a selected, single, fixed intensity of exponential function n; and
$\tau_n$: a selected, single, fixed attenuation time constant of exponential function n; and to remove said lag-behind part by using the impulse response determined by said impulse response determining means and having a single exponential function.

6. A radiographic apparatus as defined in claim 1, wherein said radiation detecting means is a flat panel X-ray detector having numerous X-ray detecting elements arranged longitudinally and transversely on an X-ray detecting surface.

7. A radiographic apparatus as defined in claim 1, wherein said apparatus is a medical apparatus.

8. A radiographic apparatus as defined in claim 7, wherein said medical apparatus is a fluoroscopic apparatus.

9. A radiographic apparatus as defined in claim 7, wherein said medical apparatus is an X-ray CT apparatus.

10. A radiographic apparatus as defined in claim 1, wherein said apparatus is for industrial use.

11. A radiographic apparatus as defined in claim 10, wherein said apparatus for industrial use is a nondestructive inspecting apparatus.

12. A radiation detection signal processing method for taking, at predetermined sampling time intervals, radiation detection signals generated by irradiating an object under examination, and performing a signal processing to obtain radiographic images based on the radiation detection signals outputted at the predetermined sampling time intervals, said method comprising the steps of:

removing lag-behind parts from the radiation detection signals by a recursive computation, on an assumption that a lag-behind part included in each of said radiation detection signals taken at the predetermined sampling time intervals is due to an impulse response formed of a plurality of exponential functions with different attenuation time constants;

determining, prior to the above removing step, an impulse response having a single exponential function from said impulse response formed of a plurality of exponential functions, based on a selected, single, fixed attenuation time constant having a single, fixed value for attenuating each of said radiation detection signals to a noise level in a radiation non-emission state following a radiation emission state; and obtaining corrected radiation detection signals by using the impulse response determined in the above determining step and removing the lag-behind parts from the radiation detection signals.

13. A radiation detection signal processing method as defined in claim 12, wherein said determining step is executed to determine said impulse response having a single exponential function by using the selected, single, fixed attenuation time constant having the single, fixed value for attenuating each of said radiation detection signals to said noise level in said radiation non-emission state following said radiation emission state, within one second of a start of said radiation non-emission state, and a selected, single, fixed intensity of the radiation.

14. A radiation detection signal processing method as defined in claim 12, wherein said determining step is executed to determine said impulse response having a single exponential function by using the selected, single, fixed attenuation time constant having the single, fixed value in a range of 0.5 seconds to 1.0 second, and a selected, single, fixed intensity of the radiation having single, fixed value for attenuating each of said radiation detection signals to said noise level in said radiation non-emission state following said radiation emission state.

15. A radiation detection signal processing method as defined in claim 12, wherein the radiation is emitted to provide a radiation emitting time in a range of five seconds to 15 seconds in said radiation emission state preceding said radiation non-emission state.

16. A radiation detection signal processing method as defined in claim 12, wherein the recursive computation for removing the lag-behind part from each of the radiation detection signals is performed based on the following equations A-C:

$$X_k = Y_k - \Sigma_{n=1}^{N} \{\alpha_n \cdot [1 - \exp(T_n)] \cdot \exp(T_n) \cdot S_{nk}\} \quad \text{A}$$

$$T_n = -\Delta t / \tau_n \quad \text{B}$$

$$S_{nk} = X_{k-1} + \exp(T_n) \cdot S_{n(k-1)} \quad \text{C}$$

where $\Delta t$: the sampling time interval;

k: a subscript representing a k-th point of time in a sampling time series;

$Y_k$: a radiation detection signal taken at the k-th sampling time;

$X_k$: a corrected radiation detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\Delta_n$: a selected, single, fixed intensity of exponential function n; and $\tau_n$: a selected, single, fixed attenuation time constant of exponential function n; and said lag-behind part is removed by using the impulse response determined in said determining step and having a single exponential function.

17. A radiation detection signal processing method as defined in claim 12, wherein a detection signal processing including said determining step is performed by using a phantom as an object, in order to determine said impulse response having a single exponential function, and a detection signal processing including said removing step and said obtaining step is performed by using the impulse response determined and the object under examination.

18. A radiation detection signal processing method as defined in claim 12, wherein said determining step includes:

repeating a series of operations for provisionally setting the selected, single, fixed attenuation time constant and a selected, single, fixed intensity constituting said impulse response, and determining whether, with the set impulse response, an attenuation to said noise level has occurred within a predetermined time, until the impulse response is found appropriate for causing an attenuation to said noise level within said predetermined time; and establishing the impulse response as valid when the impulse response is found appropriate.

19. A radiation detection signal processing method as defined in claim 12, wherein said determining step is executed by a central processing unit.

20. A radiation detection signal processing method as defined in claim 12, wherein said determining step is executed manually.

* * * * *